United States Patent [19]

Glasser et al.

[11] 4,021,862
[45] May 10, 1977

[54] RADIATION EYE SHIELD

[75] Inventors: Herman Glasser, New Hyde Park; Patrick F. Panetta, East Islip, both of N.Y.

[73] Assignee: Nuclear Associates, Inc., Carle Place, N.Y.

[22] Filed: June 2, 1975

[21] Appl. No.: 582,820

[52] U.S. Cl. .................... 2/431; 2/441; 250/516
[51] Int. Cl.² .................. A61F 9/02; G21F 3/02
[58] Field of Search ............. 2/8, 12, 14 B, 14 C, 2/14 H, 14 J; 250/515, 516, 519, 431, 441

[56] References Cited

UNITED STATES PATENTS

| 2,645,775 | 7/1953 | Splaine | 2/14 C |
| 3,052,799 | 9/1962 | Hollands | 250/516 |
| 3,267,807 | 8/1966 | Swope et al. | 2/14 J |
| 3,325,825 | 6/1967 | Christianson et al. | 2/14 H |
| 3,569,713 | 3/1971 | Via, Jr. | 250/516 |
| 3,689,136 | 9/1972 | Atamian | 2/14 J X |

OTHER PUBLICATIONS

General Electric X-Ray Corp., "The Blue Book of X-Ray Supplies," pp. 65 and 66, 1932.

Primary Examiner—Werner H. Schroeder
Assistant Examiner—Peter Nerbun
Attorney, Agent, or Firm—Lackenbach, Lilling & Siegel

[57] ABSTRACT

A radiation eye shield adapted to protect the wearer from the hazards of direct beam and scattered radiation. In one embodiment, the entire eye shield is of a high density material and in another example of the invention, the shield comprises goggles having a pair of lead-glass lenses and lead impregnated vinyl shielding applied to the front and side surfaces of the goggles surrounding the lenses.

13 Claims, 7 Drawing Figures

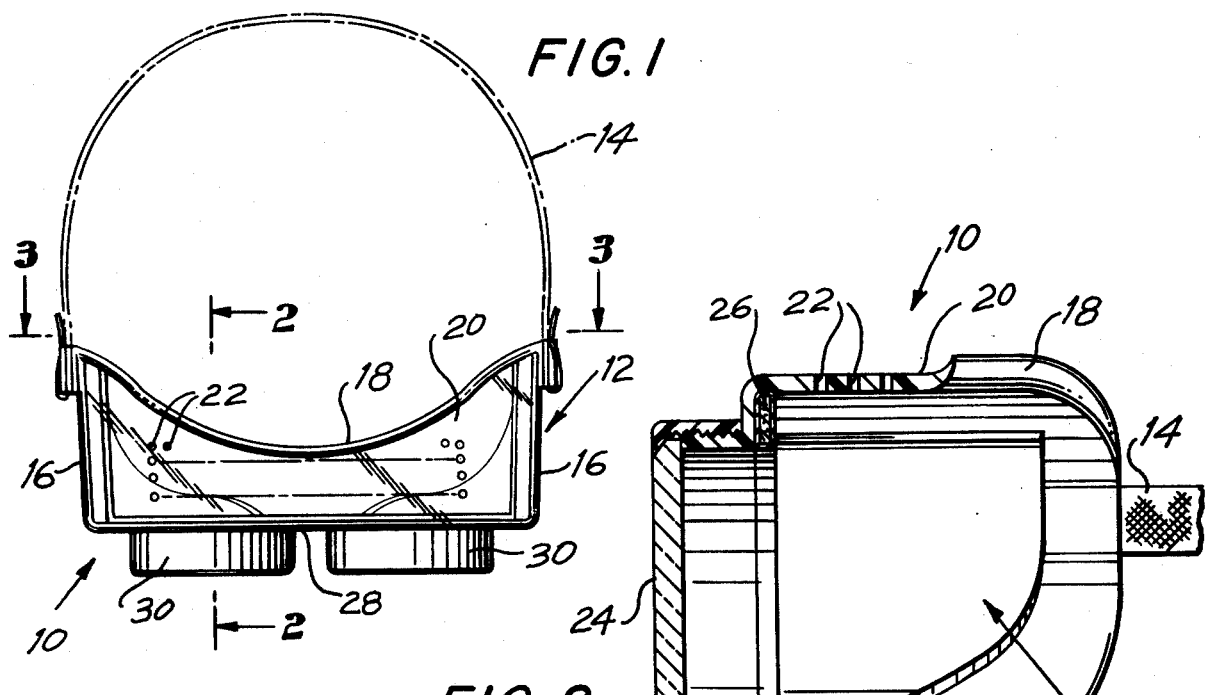
FIG. 1
FIG. 2
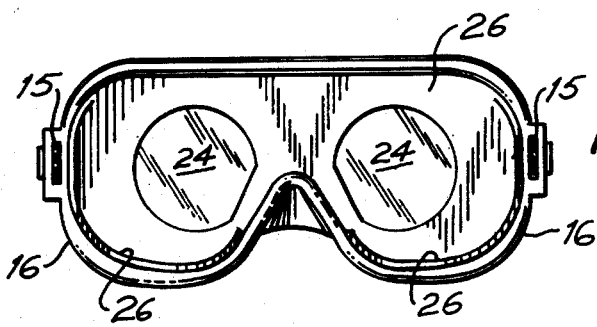
FIG. 3
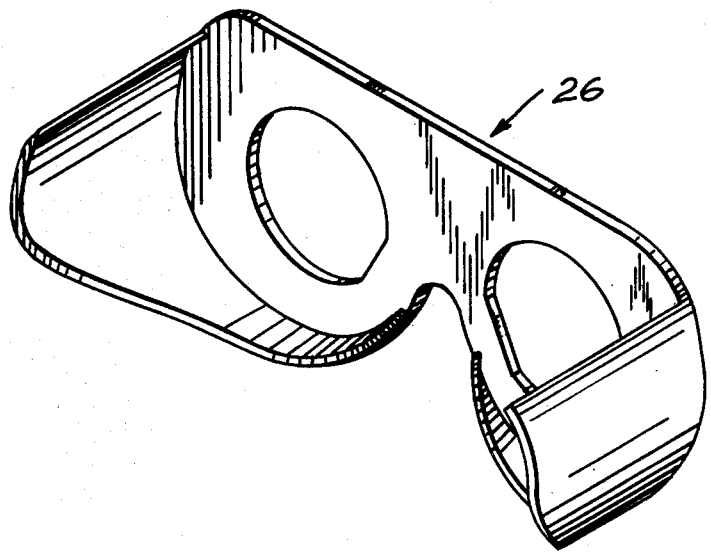
FIG. 4

RADIATION EYE SHIELD

BACKGROUND AND SUMMARY OF THE INVENTION

Exposing one's eyes to high amounts of ionizing radiation is fairly common in various trades and industries. It is especially true in the medical profession, particularly with doctors who specialize in fluoroscopic procedures including cardiac catherization. An article written by Dr. H. D. Maillie and W. D. Gregory, both of the University of Rochester School of Medicine and Dentistry, appearing in the August, 1973 issue of RADIOLOGY magazine particularly points out this problem. On page 463 the authors describe the average exposure to the eyes of cardiologists. It is also noted that, because of this exposure, they can perform only a limited number of catherizations per week. A more detailed description of this problem follows in the article. A table of findings from a controlled experiment is included on page 465. The tone on page 465 seems to indicate that the yearly exposure of cardiologists is higher than that which is recommended by the National Academy of Sciences Advisory Committee on the Biological Effects of Ionizing Radiation (the Beir Committee). In summing up, the author states, "It is felt that, until it can be established that a high threshold does exist for the radiation production of lens opacities in man, steps should be taken to prevent exposure to the eyes in excess of MPD (Maximum Permissible Dose Ionizing Radiation)." However, the authors of this article do not describe or recommend any steps or procedures which will protect the eyes from radiation.

U.S. Pat. Nos. 1,191,274 and 3,030,628 teach protective face masks and anti-ray eye shields, but neither of these patents discloses an ionizing radiation eye shield of the type described and claimed in the present patent application.

It is, therefore, the principal object of the invention to provide a novel radiation eye shield.

Another object of the invention is to provide a fluoroscopic eye shield which protects a fluoroscopist from the hazards of a direct x-ray beam or the scattered radiation emanating from the patient's body.

Yet another object of the invention is to protect the user's eyes from every angle during cardiac catherization or other lengthy procedures involving fluoroscopy.

It is a further object of the invention to provide a radiation eye shield of lightweight construction and one which remains firmly and comfortably in place during use, even if the user wears glasses.

In particular, the present invention includes a pair of radiation-attenuating goggles of a high density material or one having extra periphal shielding around the pair of lead-glass lenses. In one example, the housing or frame supporting the lenses suitably comprises the means of support for the additional shielding. However, this extra protective radiation shielding which surrounds the front and side surfaces of the goggles, may also preferably shield the eyes as well from above and below and may actually comprise the same high density material used for the lenses.

The above and other ojects of the present invention will become apparent upon reading the following specification and referring to the accompanying drawing, which forms a material part of this disclosure.

The invention accordingly consists in the features of construction, combinations of elements, and arrangements of parts which will be exemplified in the constrution hereinafter described and of which the scope will be indicated by the appended claims.

BRIEF DESCRIPTION OF THE DRAWING

FIG. 1 is a top view of the radiation or fluorscopic eye shield of the present invention;

FIG. 2 is a sectional view of the invention, taken along the line 2—2 of FIG. 1;

FIG. 3 is a sectional view of the invention, taken along the line 3—3 of FIG. 1;

FIG. 4 is a perspective view of the exta shielding, taken from the top and side, without the goggles present;

DESCRIPTION OF THE PREFERRED EMBODIMENTS

Figure 5:
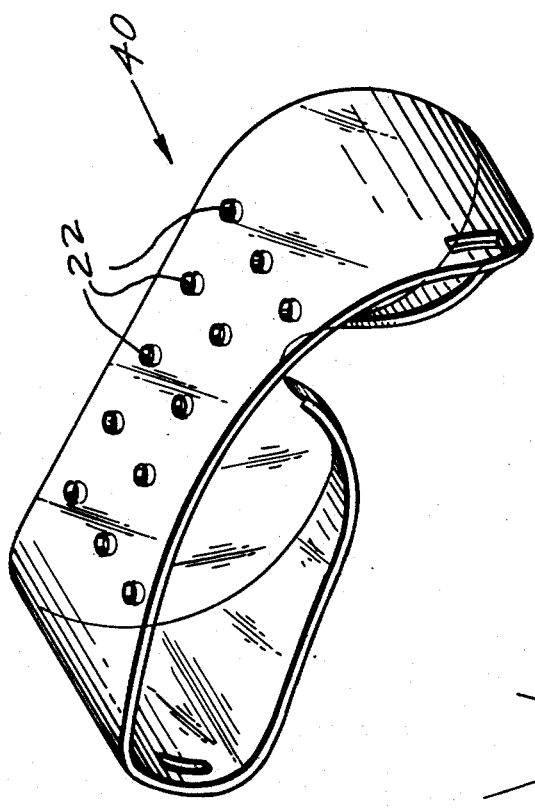
FIG. 5 is a perspective view of a modified radiation eye shield, wherein the front portion is a large viewing window and the remainder portion is the housing suporing same.

The present invention in its broadest application, therefore, comprises frame means or a housing in the form or shape of goggles having lead-glass lenses or a single large lens and wherein the frame means or housing forming the overall goggles comprises a high density material for shielding the eyes from radiation, whether scattered or from a direct beam. Thus, the basic invention may simply comprise a frame means or, preferably, housing in the form and shape of a conventional pair of goggles wherein the material forming same in simply lead, and wherein the lenses are made of a clear or transparent lead-glass material. Other suitable high density materials may be used in lieu of lead, such as tantalum, tungsten, or the like. As will be explained hereinafter in greater detail, the preferred embodiment of the invention incorporates suitable frame means or a housing supporting the lead-glass lenses or lens, wherein the frame means or housing is preferably made from a lead-vinyl material. Such material may comprise a vinyl impregnated with lead or a foam-like vinyl material containing lead, or even a laminate of lead and vinyl or other suitable material possessing effective shielding qualities, as is conventionally well known in the art.

In the drawing, and referring more particularly to FIGS. 1-4, a radiation eye shield is generally designated by the reference character 10, and comprises a suitable frame means or housing 12 having an adjustable, preferably elastic headband 14 attached to the side portions or panels 16. The headband 14 being elastic or otherwise suitably adjustable is used to accommodate the fit of the eye shield or goggles 10 on one's head. The ends of the headband 14 may be fixedly secured to the goggles 10 or may pass through a pair of suitable elongated apertures 15 (only one shown) on each side of the goggles 10 to provide even greater adjustment to the length of the headband 14. The interior edge or front portion 18 of the goggles 10 is contoured and made to fit comfortably against one's face. The top portion 20 of the goggles 10 should preferably have suitable ventilating means, such as the ventilation holes 22 to prevent fogging of the lenses 24 and to permit circulation of the ambient air.

In the particular embodiment of FIGS. 1-4, the eye shield or goggles 10 are equipped with a radiation protective shield 26 of one or more pieces secured in any suitable manner to the goggles 10, such as by means of adhesives, fasteners and the like, to the inner front, side, bottom and even top surfaces of the goggles 10. The front portion 28 of the shield 26 is, of course, provided with suitable cutouts for the eye lenses 24 and for permitting the nose to protrude from the goggles 10. A top portion of the shield 26, although not shown for purposes of convenience, may extend entirely across the roof of the shield 26, as best shown in FIG. 4, and same would also be provided with ventilation holes coincident with those in the top portion of the goggles 10. This top portion is useful for protecting the user from scattered radiation from the patient and table, particularly from scattered radiation reflected from the ceiling and x-ray machine fixtures disposed above and about the user.

As noted hereinbefore, the shield 26 may comprise the actual goggles 10 or it can be made of any suitable high density radiation protective material. The shield 26 may thus be of lead or any other radiation protective metal. The shield 26 should preferably be made of a soft flexible material, and suitably impregnated with a high density material. Such a soft flexible material is "warm to the touch" and is more comfortable to one's face, in comparison to a metal sheet material which is cold to the touch.

The preferred material for the goggles 10 itself or for the shield 26 when the goggles 10 are made of another material, such as plastic, is a lead-vinyl composite with the previously mentioned qualities. Although lead rubber may also be used in lieu thereof, this lead impregnated vinyl material is preferred inasmuch as it is 10% lighter in weight than lead rubber. Lead-impregnated vinyl has a sanitary, non-absorbing, smoothe surface on both sides and it also has an idefinite shelf life, as the material does not age. Further qualities and properties are its uniform density, flexibility and pliability. It is also acid and alkali resistant, odorless, and exhibits considerable abrasion resistance. The preferred thickness of shielding may vary over a wide range dependent upon the degree of shielding required. An example of a desired material is Lead X (manufactured by the Bar Ray Company of Brooklyn, N.Y., and Lead X is its trademark).

The goggles 10 have two apertures 27 in the front 28 thereof and extending outwardly therefrom are suitable lens housings 30, for removably replacing the lenses 24, as may be necessary if they break or otherwise are damaged during use, for instance if the goggles 10 are dropped. The housings 30 are suitably provided with external threads, and cover means 32 having compatible internal threads together hold the removable lenses 24 in place. Of course, the lenses 24 may be permanently affixed to the goggles 10, if desired. For example, if desired they may be secured directly to the shield 26 itself or to the front portion 28.

Although the lens 24 may be made from any transparent radiation protective material, it is preferred to employ a transparent lead-glass material for the lens.

If desired, the two lenses 24 may be replaced by a single elongated or wide lens (not shown) forming a large window-like structure with which to look and observe through. Such a structure would provide greater peripheral vision than that of a pair of lenses. Also, these lenses may be angulated and joined at the center by a flexible bond such that they bridge the nose. The lens structure may also be comprised of a composite of lenses completely abridging the eyes and temples to provide further peripheral vision. Such a structure is shown in FIG. 5, where the shield itself is the housing or goggle means, and the front panel is a single large lens, and the radiation eye shield or actual goggles 40 themselves form the extra radiation shielding in these alternate constructions where the material forming the goggles is of high density. For example, the goggles 40 of FIG. 5 may comprise elements of leadglass fixedly held together by conventional adhering means or other securing means, or the goggles could be made in one piece, although it would be expensive to do so.

Figure 7:
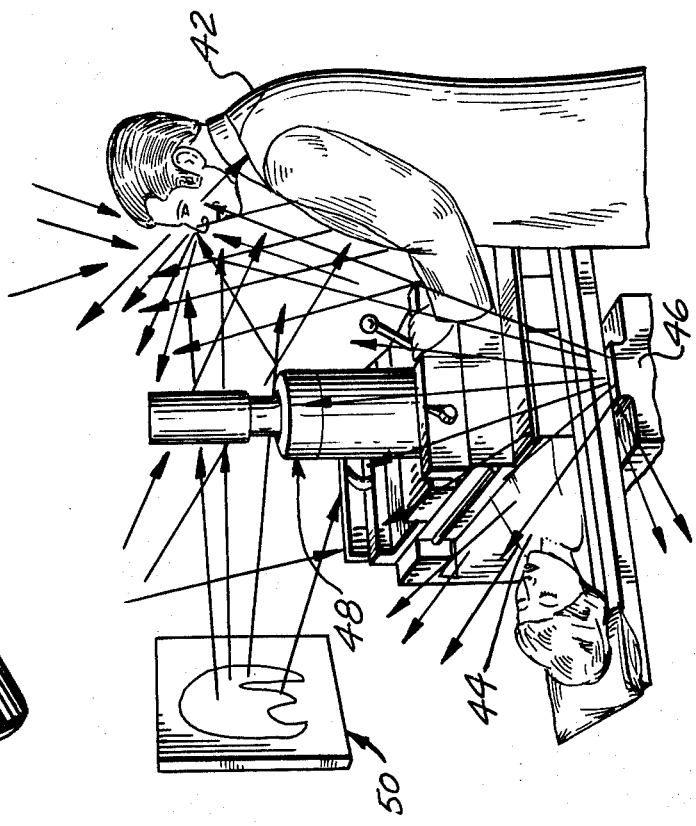
FIGS. 6 and 7 are perspective views of a fluoroscopist, respectively, showing him with and without the goggles and a dramatization of the ionizing radiation impinging upon his eyes, during ordinary fluoroscopic procedures.
Figure 6:
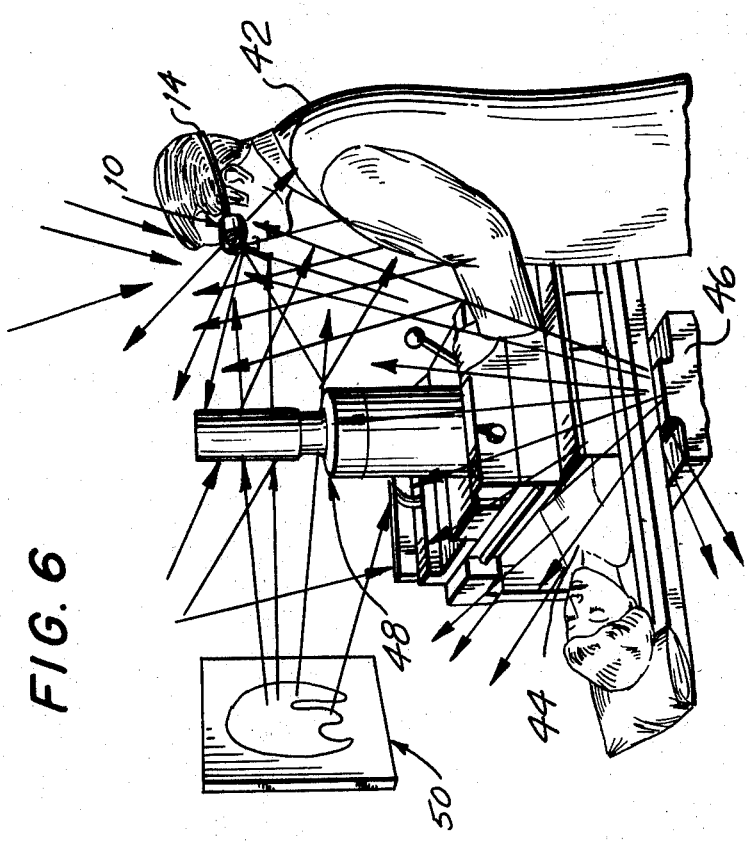

FIGS. 6 and 7 illustrate a fluoroscopist 42 conducting fluoroscopic procedures on a patient 44. The x-ray tube or device emitting x-rays 46 is below the patient and an image amplifier 48 is disposed above the patient. A TV monitor 50 may be mounted on a wall or on a cart and the arrows are representative of the ionized rays scattered about the patient and fluoroscopist during such procedures. Note that both direct and scattered rays can penetrate one's eyes, and the goggles or eye shield 10 of th present invention, as shown in FIG. 6, clearly protects the eyes from every angle, not just from rays directly impinging eyes shielded by simple lead-glass lenses alone.

While the invention has been described, disclosed, illustrated and shown in terms of an embodiment or modification which it has assumed in practice, the scope of the invention should not be deemed to be limited by the precise embodiment or modification herein described, disclosed, illustrated or shown, such other embodiments or modifications as may be suggested to those having the benefit of the teachings herein being intended to be reserved especially as they fall within the scope and breadth of the claims here appended.

What is claimed is:

1. A radiation eye shield device to be worn by a user for providing protection to said user's eyes from radiation, such as scattered radiation, comprising:

a frame having a front portion contoured to fit against said user's face, a top portion shaped to extend across the face just above the eyes of the user and connected to the top part of the front portion, a bottom portion shaped to extend across the face just below the eyes and connected to the bottom part of the front portion, said bottom portion having a contoured area to accommodate the user's nose, and side panels to cover the area bounded by the front portion, the bottom portion, the top portion and the side of the head, said side panels being connected to said front, bottom and top portions, said front portion having at least one cut-out area, so as to allow the user to see out from the frame;

a radiation shield made of a radiation shielding material and of the same general shape as said frame in close juxtaposition to the frame, said shield having at least one cutout area corresponding in location to that of said cut-out area of said frame, said shield being designed to protect the user from radiation emanating from all directions, including from above, below and from the sides in addition to direct radiation from in front of the user; and at least one transparent viewing window or lens made of a transparent radiation shielding material positioned in said cut-out area of said frame.

2. The device according the claim 1, wherein said shield and said window are made of the same radiation shielding material.

3. The device according the claim 2, wherein said shielding material is lead-glass.

4. The device according to claim 3, wherein said frame, said shield and said window form a single integral unit, so as to provide a greater peripheral viewing capability.

5. The device according to claim 1, wherein said frame and said shield form a single integral unit.

6. The device according to claim 1, wherein said shield and said window are made of different radiation shielding materials.

7. The device according to claim 6, wherein said window is made of a lead-glass material and said shield is made of a material containing lead.

8. The device according to claim 7, wherein said material containing lead is a lead-vinyl material.

9. The device according the claim 1, wherein said frame is further provided with an adjustable headband.

10. The device according to claim 1, wherein said frame is further provided with a plurality of ventilation apertures.

11. The device according to claim 10, wherein said shield is provided with a plurality of ventilation apertures positioned on the shield in such a manner as to correspond to the locations of the apertures provided on the frame.

12. The device according to claim 1, including a pair of transparent lead-glass lenses to serve as transparent viewing windows.

13. The device according to claim 12, wherein said lenses are removably mounted on said frame.

* * * * *